(12) United States Patent
Rinne et al.

(10) Patent No.: US 8,993,796 B2
(45) Date of Patent: Mar. 31, 2015

(54) PROCESS FOR THE MANUFACTURING OF VINYL ACETATE

(75) Inventors: Bernd Rinne, Lingen (DE); Stefan Hess, Gross-Gerau (DE); Ali Hotaman, Frankfurt (DE); Michael J. Bayer, Eschborn (DE); Berthold Nuber, Kronberg (DE)

(73) Assignee: Celanese International Corporation, Irving, TX (US)

( * ) Notice: Subject to any disclaimer, the term of this patent is extended or adjusted under 35 U.S.C. 154(b) by 954 days.

(21) Appl. No.: 13/139,289

(22) PCT Filed: Nov. 28, 2009

(86) PCT No.: PCT/EP2009/008485
§ 371 (c)(1),
(2), (4) Date: Oct. 21, 2011

(87) PCT Pub. No.: WO2010/066352
PCT Pub. Date: Jun. 17, 2010

(65) Prior Publication Data
US 2012/0136170 A1     May 31, 2012

Related U.S. Application Data

(60) Provisional application No. 61/203,226, filed on Dec. 18, 2008.

(30) Foreign Application Priority Data

Dec. 18, 2008   (EP) .................................... 08021694

(51) Int. Cl.
C07C 67/48     (2006.01)
C07C 67/055    (2006.01)
C07C 67/58     (2006.01)

(52) U.S. Cl.
CPC .............. C07C 67/055 (2013.01); C07C 67/58 (2013.01)
USPC ......................................................... 560/248

(58) Field of Classification Search
USPC ......................................................... 560/248
See application file for complete search history.

(56) References Cited

U.S. PATENT DOCUMENTS

| | | | |
|---|---|---|---|
| 2,425,389 A | | 8/1947 | Oxley et al. |
| 4,156,632 A | * | 5/1979 | Roscher et al. ................. 203/14 |
| 4,818,347 A | | 4/1989 | Roscher et al. |
| 5,066,365 A | * | 11/1991 | Roscher et al. ................. 203/42 |
| 5,719,315 A | | 2/1998 | Tustin et al. |
| 6,121,498 A | | 9/2000 | Tustin et al. |
| 6,342,628 B1 | | 1/2002 | Williams et al. |
| 2007/0032678 A1 | | 2/2007 | Stamm et al. |

FOREIGN PATENT DOCUMENTS

| | | |
|---|---|---|
| DE | 3422575 A1 | 12/1985 |
| EP | 0423658 A2 | 4/1991 |
| EP | 0539274 | 4/1993 |
| EP | 1760065 A1 | 3/2007 |
| RU | 2223942 | 2/2004 |

OTHER PUBLICATIONS

Tustin, et al., "Synthesis of vinyl acetate monomer from synthesis gas", Catalysis Today, vol. 58, No. 4, pp. 281-291 (2000).
Roscher, Ullman's Encyclopedia of Industrial Chemistry, pp. 1-18.
Pestman et al., Reactions of Carboxylic Acids on Oxides, Journal of Catalysis 168:255-264 (1997).
Decision on Grant for Russian Application No. 201112887104 dated Oct. 3, 2012.

* cited by examiner

*Primary Examiner* — Joseph Kosack
*Assistant Examiner* — Amanda L Aguirre

(57) ABSTRACT

The present invention relates to a process for the separation of vinyl acetate from a gas mixture formed by the reaction of ethylene with acetic acid and oxygen in the gas phase over catalysts comprising palladium or palladium compounds.

23 Claims, 1 Drawing Sheet

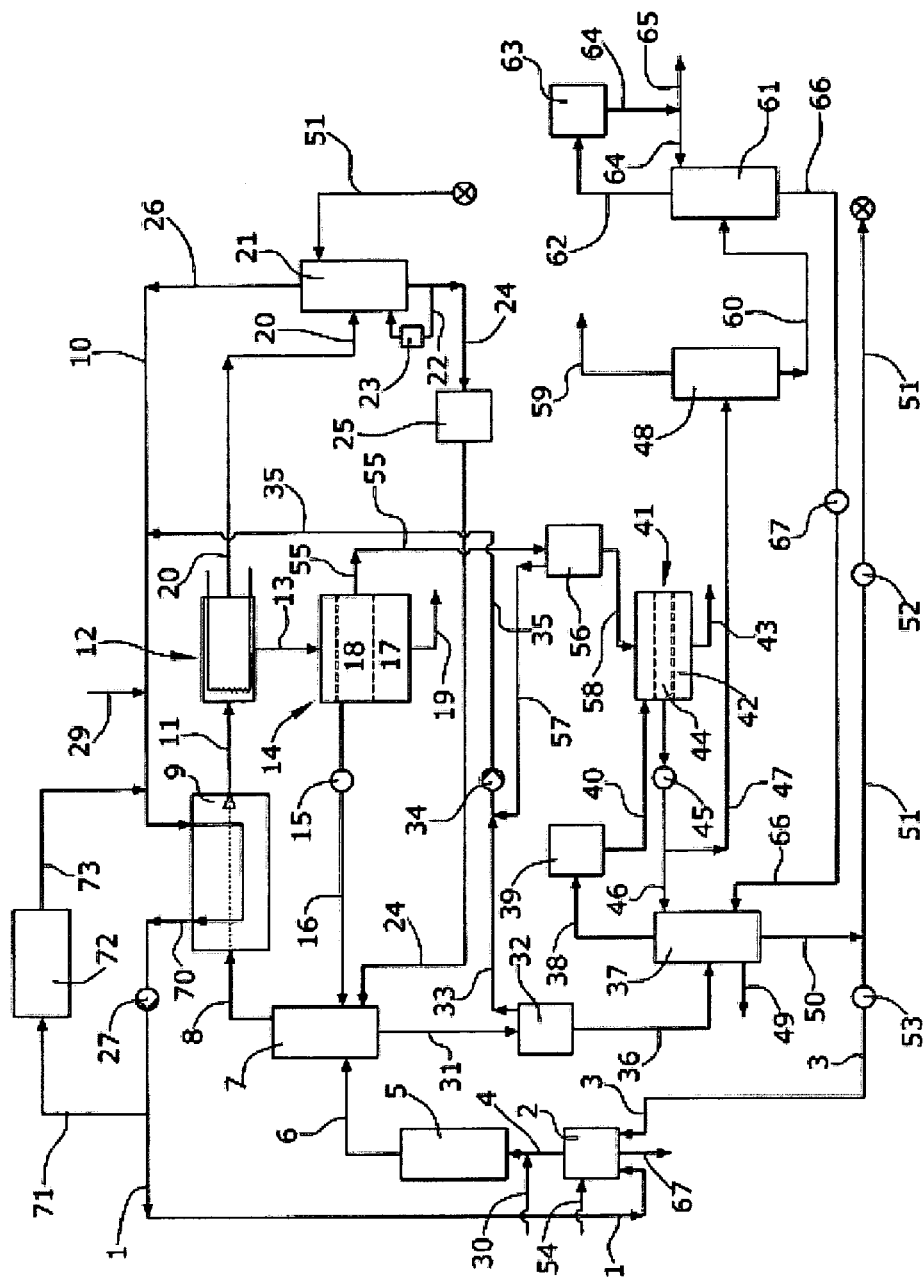

PROCESS FOR THE MANUFACTURING OF VINYL ACETATE

CROSS-REFERENCE TO RELATED APPLICATIONS

The present Application is a U.S. national phase of PCT/EP2009/008485, filed on Nov. 28, 2009 ("PCT Application"), which claims priority from European Application No. 08021694.8 filed on Dec. 13, 2008, and U.S. Provisional Application No. 61/203,226 filed on Dec. 18, 2008 all of which are hereby incorporated by reference in their entirety into the present Application.

The present invention relates to a process for the separation of vinyl acetate from a gas mixture formed by the reaction of ethylene with acetic acid and oxygen in the gas phase over catalysts comprising palladium or palladium compounds.

The preparation of vinyl acetate by reaction of ethylene with acetic acid and oxygen or oxygen-containing gases in the gas phase over fixed-bed catalysts is already known. The reaction is generally carried out at pressures of from 1 to 2.5 MPa and temperatures of from 100 to 250° C. Suitable catalysts comprise a noble metal component and an activator component. The noble metal component comprises palladium and/or compounds thereof; in addition, gold or its compounds can also be present. The activator component comprises compounds of elements of the $1^{st}$ main group and/or the $2^{nd}$ main group and/or cadmium. These active components are applied to supports in finely divided form, with silica or aluminum oxide generally being used as support material.

In general, the palladium content of the catalyst is from 0.5 to 5% by weight. If gold or one of its compounds is used, it is added in a proportion of from 0.01 to 4% by weight.

Each individual activator is likewise generally added in a proportion of from 0.01 to 4% by weight. In the case of all three percentages indicated, the metal part of the component is in each case based on the total mass of the supported catalyst. Preference is given to the following catalysts: palladium/alkali element/cadmium and palladium/gold/alkali element, with palladium and gold being able to be present as metals or compounds in the finished catalyst and potassium being preferred as alkali element. Potassium is used in the form of a carboxylate, in particular as acetate.

Particular preference is given to the catalysts palladium acetate/potassium acetate/cadmium acetate and palladium acetate/barium acetoaurate/potassium acetate.

In the multistage catalytic process, vinyl acetate and water are formed in equimolar amounts, as shown in the following overall equation:

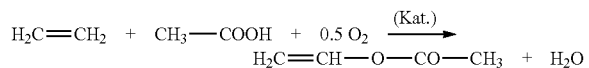

The total oxidation of ethylene, which cannot be entirely avoided, forms $CO_2$ and water:

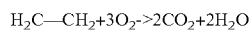

More than 1 mol of water is thus obtained per mole of vinyl acetate; in general, the weight of water is about one quarter of the weight of the vinyl acetate formed.

Apart from $CO_2$, small amounts of other by-products, including ethyl acetate, are formed in a proportion of about 1000-2000 ppm by weight, based on the vinyl acetate formed.

Only a small amount of not more than 250 ppm by weight of ethyl acetate is permitted in the pure vinyl acetate. The removal of vinyl acetate requires a large amount of energy and the prior art addresses various methods of reducing the energy consumption in the purification of vinyl acetate with removal of ethyl acetate and other by-products.

The mixture used for the reaction contains a multiple of the stoichiometrically required amount of ethylene. Accordingly, the ethylene conversion is relatively low (about 10%) and the unreacted ethylene has to be recirculated to the reaction zone. Vinyl acetate is usually separated off from the mixture of gaseous reaction products in a multistage process.

In the process described in DE-A1-34 22 575, the hot gas mixture leaving the vinyl acetate reactor, which consists essentially of ethylene, acetic acid, vinyl acetate, water, carbon dioxide, oxygen and inerts such as, for example, nitrogen and argon and contains ethyl acetate is introduced into a first distillation column which operates without additional heating, known as the predewatering column.

The gas mixture leaving the top of this column is firstly brought into contact with the reflux to the predewatering column in a heat exchanger, resulting in the gas mixture being cooled and particuarly condensed and the reflux being correspondingly heated. The gas mixture subsequently goes from the heat exchanger to a condenser. The material which is liquefied here is collected in a collection vessel where separation into an aqueous phase and an organic phase occurs. The aqueous phase is discharged while all or part of the organic phase is recirculated as reflux to the top of the predewatering column.

The material which has not been liquefied in the condenser comprises still gaseous vinyl acetate. This is scrubbed out of the gas mixture in a scrubbing column operated using acetic acid as scrubbing liquid, known as the circulating gas scrubber or "recycle gas scrubber". The remaining tailgas is recirculated to the reactor. The outflow from the bottom of the recycle gas scrubber and the remainder of the liquefied organic phase from the condensate of the predewatering column is collected in a further vessel if not all of the liquefied organic phase from the condensate is used as reflux to the predewatering column.

A mixture comprising vinyl acetate, acetic acid and about half of the water of reaction and also by-products is obtained at the bottom of the predewatering column. The other half of the water of reaction has already been separated off without introduction of energy and forms the aqueous phase of the condensate formed on cooling of the vapor from the top of the predewatering column.

The bottom product from the predewatering column is firstly fed into a collection vessel, also referred to as the crude vinyl acetate collection vessel, and subsequently worked up in a second distillation column, known as the azeotrope column. Vinyl acetate saturated with water is obtained as overhead product, and a side stream comprising ethyl acetate and a bottom product which is recirculated to the system as recycle acetic acid are obtained. The side stream comprising ethyl acetate is discharged. The vinyl acetate saturated with water which is not returned as reflux to the top of the second distillation column is combined with the remainder of the liquefied organic phase from the condensate from the predewatering column.

The mixture is subsequently fed to a further, third distillation column, known as the dewatering column. The vapor from the top of this column is, after condensation, virtually entirely recirculated as reflux. The side offtake stream is separated into an aqueous phase and an organic phase, with the aqueous phase then being discharged and the organic phase being returned to the column. A dry vinyl acetate is taken off at the bottom of the dewatering column and fed to a further, fourth column, known as the pure vinyl acetate column. In this column, vinyl acetate which is virtually free of ethyl acetate is obtained as overhead product, while the bottoms from this column, which comprise high boilers and traces of vinyl acetate and ethyl acetate, are, after discharge of a substream, recirculated to the process.

A further variant of the known process for working up vinyl acetate is known from EP-A2-0 423 658. In this variant, the bottom product from the recycle gas scrubber is not combined directly with the water-containing vinyl acetate obtained in the azeotrope column but is firstly introduced into a further column in which a vinyl acetate/water azeotrope is obtained as overhead product and acetic acid, which is recirculated to the process, is obtained as bottom product. Aqueous vinyl acetate obtained in this additional column is combined with the vinyl acetate saturated with water obtained from the azeotrope column and is worked up by a method corresponding to the process of DE-A1-34 22 575 in the downstream dewatering column and pure vinyl acetate column. The process of EP-A2-0 423 658 requires about the same distillation energy for separating off ethyl acetate as does the process of DE-A1-34 22 575, but requires a smaller amount of plates in the column, which incurs lower capital costs. The uncondensed part of the vinyl acetate from the predewatering column, which is scrubbed out by means of acetic acid in the recycle gas scrubber and is obtained as acetic-acid solution, and the organic phase of the condensate from the predewatering column contain virtually no ethyl acetate and an energy-intensive removal of ethyl acetate from these vinyl acetate streams becomes unnecessary. However, this process variant requires operation of an additional distillation column for fractionating the outflow from the bottom of the recycle gas scrubber.

The known work-up processes for recovering pure vinyl acetate still have some disadvantages. Thus, the outflow from the bottom of the recycle gas scrubber and the outflow from the bottom of the predewatering column contain considerable amounts of gases, especially ethylene, in dissolved form. The depressurization of the outflow from the bottom of the predewatering column and from the recycle gas scrubber in the crude vinyl acetate collection vessel therefore liberates an appreciable amount of recycle gas which has to be compressed in a recycle gas compressor with a high consumption of energy before it can be returned to the reaction circuit. In general, the crude vinyl acetate is depressurized from a pressure in the range from 0.5 to 2.0 MPa to a pressure in the range from 0.02 to 0.2 MPa. The gas formed in the depressurization comprises predominantly ethylene and also carbon dioxide, nitrogen and further inerts such as argon and also organic constituents such as acetic acid and small amounts of vinyl acetate and ethyl acetate. This gas is also referred to as recycle gas which is recirculated to the process.

A characteristic of the known work-up process is the combination of the acetic-acid solution obtained from the outflow from the bottom of the recycle gas scrubber with the vinyl acetate saturated with water from the overhead product of the azeotrope column and the remainder of the liquefied organic phase from the condensate from the predewatering column. For this reason, an acetic-acid mixture, from which acetic acid has to be separated off with a high consumption of energy, is passed to the further purification stages occurring in the downstream dewatering column and pure vinyl acetate column. In addition, the dewatering column and the pure vinyl acetate column have to be constructed using corrosion-resistant materials which are not sensitive to acetic acid.

Likewise, the condensate from the predewatering column which is not returned as reflux to the top of the predewatering column still contains a certain amount of ethyl acetate. Since this stream is combined only after the azeotrope column with the vinyl acetate saturated with water obtained as overhead product there, the downstream dewatering column and pure vinyl acetate column are supplied with a stream which contains ethyl acetate and from which ethyl acetate can be separated off only with high consumption of energy.

Finally, improved removal of water and ethyl acetate in a step which is as early as possible in the work-up process is desirable to reduce the amount of these undesirable materials carried through the overall work-up process as much as possible and to avoid the associated, energy-intensive removal in the pure vinyl acetate distillation.

EP 1 760 065 A1 discloses a process for isolating vinyl acetate from a gas mixture formed in the reaction of ethylene with acidic acid and oxygen in the gas phase over catalysts comprising palladium or palladium compounds, with recirculation of the acidic acid solution obtained in the recycle gas scrubber to the first distillation column (predewatering column). However, the process disclosed in EP 1 760 065 A1 is very energy consuming since the gas stream which enters the acidic acid vaporizer has to be heated to temperatures about 120 to 130° C. Moreover, steam consumption, in particular in the azeotropic column is high.

Therefore, it was an object of the present invention to overcome the problems present in the prior art and in particular, it was an object to significantly reduce the energy and steam consumption of the overall process for the manufacturing of vinyl acetate.

The invention accordingly provides a process for the separation of vinyl acetate from a gas mixture formed by the reaction of ethylene with acetic acid and oxygen in the gas phase over catalysts comprising palladium or palladium compounds comprising a) introducing said gas mixture leaving the vinylacetate reactor into a predewatering column, b) cooling the gas mixture leaving the top of dewatering column below 85° C., preferably to a temperature below 80° C. and most preferably to a temperature between 55° C. and 75° C. in a countercurrent heat exchanger, c) further cooling the gas mixture or the gas and liquid mixture leaving the heat exchanger in step b) to from −20 to 50° C. with the condensate obtained separating into an aqueous phase and an organic phase, d) taking off the water phase formed in step c), e) recirculating all or part of the organic phase formed in step c) as reflux to the top of the dewatering column utilized in step a) and taking off part of the organic phase which is not used as reflux, f) scrubbing the gas comprising vinyl acetate which is not condensed in step b) in a gas scrubbing column by means of an aqueous acetic acid solution, g) isolating the vinyl acetate, h) heating the recycle gas leaving the scrubbing column, optionally together with fresh ethylene and/or recycle gas coming from a $CO_2$ removal system and/or flash gas in the countercurrent heat exchanger and thereby reducing the temperature of the gas mixture leaving the top of the dewatering column, and i) introducing the recycle gas optionally together with fresh ethylene and/or recycle gas coming from a $CO_2$ removal system and/or flash gas preheated in step h) into the vinyl acetate reactor.

In step a), the gas mixture leaving the reaction zone is preferably firstly cooled to from 100° C.-150° C., more preferably from 110 to 140° C. In general, in this step, no condensation of the liquefiable components occurs and the gas mixture is introduced into the first distillation column, also known as predewatering column.

In step b) the gas mixture leaving the top of the first distillation column (predewatering column) is cooled below 85° C., preferably below 80° C. and most preferably between 55° C. and 75° C. in a countercurrent heat exchanger also known as a process to process heat exchanger. The gas mixture leaving the top of the first distillation column is transferred to the heat exchanger where it is subjected to countercurrent heat exchange with the gas stream comprising the recycle gas optionally together with fresh ethylene and/or recycle gas coming from a $CO_2$ removal system and/or flash gas. The cooled gas stream can partly lead to a condensation of vinylacetate.

In step c) the gas mixture or the gas and liquid mixture leaving the countercurrent heat exchanger is further cooled to from −20 to 50° C., preferably −10 to 40° C. with the condensate obtained separating into an aqueous phase and an organic phase. Cooling step c) is preferably conducted in a water-cooled condenser.

According to a preferred embodiment the process according to the present invention is conducted with a water-cooled condenser in which the gas mixture or the gas and liquid mixture is cooled to less than 35° C.

In step d) the water phase formed in step c) is taken off. The separation of the aqueous phase and the organic phase is preferably conducted in a phase separator where the material liquefied in step c) is collected. The proportion of liquid exceeding a particular level in the phase separator is conveyed back into the first distillation column (predewatering column). Once the condensate obtained in the phase separator separates into two phases, of which the aqueous phase is discharged and the organic phase is partly transferred as reflux to the top of the predewatering column and partly taking off.

In step e) of the process according to the present invention the organic phase formed in step c) is recirculated partly or completely as reflux to the top of the dewatering column utilized in step a) and, furthermore, the part of the organic phase which is not used as reflux is taking off.

In a preferred embodiment the part of the organic phase which is not used as reflux in step e) is transferred to a depressurization vessel.

In step f) the gas comprising vinyl acetate which is not condensed in step b) is scrubbed in a gas scrubbing column by means of an aqueous acidic acid solution. In a preferred embodiment the bottoms of the gas scrubbing column used in step f) are separated with a substream and recirculated with cooling by means of a heat exchanger to the lower part of the recycle gas scrubber and preferably the other part of the bottoms are conveyed through a heat exchanger in which the bottoms are heated to at least 30° C., preferably from 60 to 120° C. The heated bottom product is preferably conveyed to the lower part of the predewatering column, preferably at the $2^{nd}$ to $15^{th}$ plate, calculated from the bottom.

In step g) the vinyl acetate is isolated.

In step h) the recycle gas leaving the scrubbing column, optionally together with fresh ethylene and/or recycle gas coming from a $CO_2$ removal system and/or flash gas is heated in the countercurrent heat exchanger whereby the temperature of the gas mixture leaving the top of the first distillation column (predewatering column) is reduced.

According to a preferred embodiment the stream which enters the countercurrent heat exchanger in step h) has a temperature of 10 to 60° C., preferably 20 to 40° C. In a further preferred embodiment the stream which enters the countercurrent heat exchanger in step h) comprises fresh ethylene having a temperature before entering the stream of −20 to 40° C., preferably −20 to 10° C.

The preheated stream in step h) leaving the countercurrent heat exchanger has a temperature of 50 to 90° C., preferably 65 to 80° C.

Preferably, a part of the preheated stream in step h) leaving the countercurrent heat exchanger is removed as off gas to discharge $CO_2$ in a $CO_2$ removal system.

The carbon dioxide removal system comprises a washing step wherein the removed off gas (exhaust) containing carbon dioxide is submitted to an aqueous, alkaline solution for removal of the carbon dioxide. Such kind of exhaust washing steps are known in the art. Carbon dioxide first is absorbed in an aqueous pot ash solution and is thus removed from the exhaust. In a subsequent desorption step, the pot ash solution is regenerated by raising the temperature to 100 to 120° C. The hot aqueous pot ash solution is past back to the absorber section, and at the head of the desorber water-separated carbon dioxide is removed at a temperature of preferably 90 to 120° C. and at a pressure of, preferably 0.1 to 0.12 MPa.

To avoid the introduction of water vapor in the recycle gas the recycle gas with reduced amount of $CO_2$ leaving the $CO_2$ removal system is cooled, preferably to a temperature of 10 to 60° C., more preferably 20 to 40° C.

According to a preferred embodiment the gas stream leaving the $CO_2$ removal system and which enters the rerecycle gas stream has a temperature of 10 to 60° C., preferably 20 to 40° C.

According to a preferred embodiment of the process according to the present invention the preheated stream in step h) leaving the countercurrent heat exchanger enters the recycle gas compressor, preferably directly, from the suction side.

In step i) the recycle gas optionally together with fresh ethylene and/or recycle gas coming from a $CO_2$ removal system and/or flash gas preheated in step h) is introduced into the vinyl acetate reactor.

According to a further preferred embodiment the liquid obtained at the bottom of the predewatering column (first distillation column) which essentially comprises vinyl acetate, acidic acid, water and ethyl acetate is depressurized to a pressure of from 0.02 to 0.2 MPa, preferably 0.1 to 0.15 MPa to form flash gas. In a further embodiment the depressurized liquid is introduced in an azeotrop distillation column.

The amount of organic phase formed in step c) is dependent on the temperature to which cooling is carried out in this step. That part of the organic phase from step c) which is not utilized as reflux for step e) is taken off and preferably depressurized from a pressure of from 0.5 to 2.0 MPa to a pressure of from 0.02 to 0.2 MPa, preferably to from 0.1 to 0.15 MPa. The liquid thus obtained is preferably combined with the organic phase from the condensed overhead product from the second distillation column, also referred to as azeotrope column. The two organic phases are preferably combined in the phase separator of the azeotrope column. The proportion of the organic phase which is not returned as reflux to the top of the azeotrope column is preferably introduced into a third distillation column, also referred to as dewatering column.

The cooling temperature in step c) and the proportion of the organic phase formed in c) which is utilized as reflux in step e) are preferably selected in a manner that very little vinyl acetate but preferably all of the ethyl acetate are present in the bottom product of step a).

A preferred mode of operation according to the invention is the operation of the scrubbing column used in step f) and the recirculation of the outflow from the bottom of the scrubbing column to the lower part of the first distillation column used in step a). Part of the bottoms from the scrubbing column, also referred to as recycle gas scrubber, is circulated by pumping, with the part of the bottom product from the scrubbing column which is conveyed around the pumped circuit being cooled. Cooling of the bottom product is carried out using means with which those skilled in the art are familiar, for example heat exchangers. Preferably, the part of the bottom product which is not conveyed around the pumped circuit is taken off from the scrubbing column, heated to a temperature of at least 30° C., preferably from 60° C. to 120° C., in particular from 60° C. to 100° C., and fed into the lower part of the first distillation column used in step a). To effect heating, the bottom product pumped off from the scrubbing column is advantageously passed through a heat exchanger.

The heated bottoms from step f) are preferably fed into the first distillation column at the $2^{nd}$ to $15^{th}$ plate, in particular the $5^{th}$ to $10^{th}$ plate, calculated from the bottom of the column.

As a result of the recirculation of the heated bottom product from the scrubbing column in step f) to the lower part of the first distillation column used in step a), the temperature of the outflow from the bottom of the scrubbing column, whose temperature without this measure is generally from 30 to 50° C., is significantly increased. Here, in a first step, the bottoms are preferably firstly heated, for example in a heat exchanger, to a temperature of at least 30° C., preferably from 60° C. to 120° C. and in particular from 60° C. to 100° C. When the resulting heated bottoms from the recycle gas scrubber are fed into the lower part of the first distillation column, this stream is heated again, generally to a temperature of from 80° C. to 150° C., which also corresponds to the temperature of the bottoms from the first distillation column. This heating of the bottoms from the scrubbing column reduces the solubility of the gaseous components in the acetic-acid, crude vinyl acetate. The gaseous components, in particular ethylene and carbon dioxide, are driven off to a greater extent via the top of the first distillation column and are returned to the gas circuit at a very early point of the work-up process. The depressurization of the crude product therefore results in formation of less gas. The depressurization is preferably carried out in a collection vessel, also referred to as crude vinyl acetate collection vessel, from a pressure of from 0.5 to 2.0 MPa to a pressure of from 0.02 to 0.2 MPa, preferably to from 0.1 to 0.15 MPa. The gas obtained in the depressurization is also referred to as recycle gas (flash gas) and comprises predominantly ethylene and additionally carbon dioxide and further inerts such as nitrogen and argon and also organic constituents such as acetic acid and small amounts of vinyl acetate and ethyl acetate. A smaller amount of energy is therefore required in the recirculation of the recycle gas to the process in order to compress the recycle gas to the pressure of the reactor again. Preferably, some of the load is therefore taken off the recycle gas compressor by the recirculation of the bottoms from the scrubbing column in step f), which leads to a significant energy saving.

Furthermore, the introduction of the acetic-acid solution from the scrubbing column into the lower part of the first distillation column, preferably at the $2^{nd}$ to $15^{th}$ plate, in particular the $5^{th}$ to $10^{th}$ plate, calculated from the bottom of the column, achieves a scrubbing effect. Ethyl acetate is scrubbed into the bottom of the first distillation column and discharged via the bottom.

Vinyl acetate is present in the bottom product from the first distillation column, in the acetic-acid scrubbing solution which is formed in step f) and is preferably recirculated to the lower part of the first distillation column and in the part of the organic phase formed in step c) which is not utilized as reflux in step e). The vinyl acetate content of these three streams depends on the mode of operation of the plant and is not critical for carrying out the process of the invention.

The overhead product from the first distillation column contains only very small amounts of ethyl acetate, and the reflux recirculated in step e) and the part of the organic phase which is not used as reflux are low in ethyl acetate and can be processed further without further measures which require removal of ethyl acetate. For this purpose, the organic phase which is taken off is preferably depressurized and the liquid obtained is preferably combined with the organic phase which is obtained from the overhead product from the second distillation column, also referred to as azeotrope column. Part of the combined organic phases is recirculated as reflux to the top of the azeotrope column. The remainder is fed to the third distillation column, also referred to as dewatering column.

The gas obtained in the depressurization is also referred to as recycle gas. The recycle gas (flash gas) streams are preferably combined, then compressed in a recycle gas compressor and subsequently recirculated to the process. The purified recycle gas is advantageously combined with the tailgas obtained in the acetic acid scrub in step f), which is also referred to as recycle gas.

In a preferred embodiment of the process according to the present invention the recycle gas is combined with fresh ethylene and/or recycle gas coming from a $CO_2$ removal system. The combination of the cooled gas streams with the recycle gas leaving the scrubbing column has the advantage that the countercurrent heat exchanger cools the gas stream coming from the first distillation column more effectively. This leads to an significant energy savings.

Furthermore, the cooled gas streams comprising recycle gas leaving the scrubbing column and optionally comprising fresh ethylene and/or recycle gas coming from a $CO_2$ removal system and/or flash gas enter the countercurrent heat exchanger and are preheated. The preheated gas mixture enters the recycle gas compressor from the suction side and is further transferred to the vinyl acetate reactor. Since the gas mixture is already preheated significant energy savings can be achieved.

Preferably, at least part of the bottom product from the second distillation column (azeotropic column) is used in the gas scrub of step f). The bottom product comprises mainly acetic acid and contains not more than 10% by weight of water. Part of the bottom product which is not required in step f) is preferably recirculated to the reactor as recycle acetic acid after a small part has been discharged to remove high boilers and polymers.

In a preferred embodiment of the process of the present invention the bottoms from the third distillation column, which consist essentially of dry vinyl acetate, are fed into a fourth distillation column, known as the pure vinyl acetate column, from which pure vinyl acetate is taken off as overhead product.

The first, second, third and fourth distillation columns utilized in the work-up process for vinyl acetate are operated at temperatures, pressures and reflux ratios appropriate for the utilization of the capacity of the plant.

A preferred embodiment of the process of the invention is illustrated by means of The figure measures known per se, e.g. addition of stabilizer, are not shown.

REFERENCE SIGNS (1) line for recycle gas
(2) acetic acid vaporizer (3) line for acetic acid
(4) steam-heated line
(5) vinyl acetate reactor
(6) line
(7) predewatering column
(8) line for the vapour from the top of (7)
(9) heat exchanger
(10) line for the combined gas from (26), (29) and (73)
(11) line
(12) water-cooled condenser
(13) line for the liquefied material
(14) phase separator
(15) pump
(16) line
(17) aqueous phase
(18) organic phase
(19) line for the aqueous phase
(20) line for gas
(21) recycle gas scrubber
(22) line
(23) heat exchanger
(24) line
(25) heat exchanger
(26) line for tail gas
(27) recycle gas compressor
(29) line for ethylene
(30) line for oxygen
(31) line for liquid obtained at the bottom of (7)
(32) crude vinyl acetate collection vessel
(33) line for flash gas
(34) flash gas compressor
(35) line for the flash gas
(36) line for the organic phase obtained after depressurization
(37) second distillation column/azeotrope column
(38) line for the vapour from the top of (37)
(39) condenser
(40) line for the condensate fed
(41) phase separator
(42) aqueous phase
(43) line for aqueous phase
(44) organic phase
(45) pump
(46) line for the organic phase
(47) line for the part which is not used as reflux
(48) third distillation column
(49) line for ethyl acetate
(50) line for aqueous acetic acid
(51) line
(52) pump
(53) pump
(54) line for acetic acid
(55) line for organic phase
(56) depressurization vessel
(57) line for recycled gas
(58) line for the organic phase
(59) line for low boilers and residues of water
(60) line vinyl acetate
(61) fourth distillation column
(62) line for vapour from (61)
(63) condenser
(64) line for vinyl acetate
(65) line for pure vinyl acetate
(66) line for the bottom product of (61)
(67) pump
(70) line for preheated gas from (9)
(71) line to the $CO_2$ removal system
(72) $CO_2$ removal system (Scrubber/Absorber)
(73) line for recycle gas with reduced amount of $CO_2$ The recirculated gas mixture comprising ethylene, oxygen and $CO_2$ and also inerts and small amounts of organic components such as acetic acid, also referred to as recycle gas, is introduced via line (1) into an acetic acid vaporizer (2) configured as a tray column in which the gas stream is laden with acetic acid which is fed in via line (3). The gas mixture leaving the acetic acid vaporizer (2) is fed via a steam-heated line (4) to the vinyl acetate reactor (5). Fresh oxygen is introduced via line (30).

The gas mixture leaving the vinyl acetate reactor (5), which consists essentially of ethylene, acetic acid, vinyl acetate, water, carbon dioxide, oxygen and inert gases such as nitrogen and argon, is introduced via line (6) into the first distillation column, the predewatering column (7). The predewatering column (7) has a design known per se.

The gas mixture leaving the top of the predewatering column (7) goes via line (8) to a heat exchanger (9) where it is subjected to countercurrent heat exchange with the gasstream which enters via line (10) and is returned as preheated recycle gas via line (70) to the recycle gas compressor (27). In the countercurrent heat exchanger (9) the gas stream which enters via line (10) and which is returned as preheated recycle gas via line (70) is not mixed with the gas mixture leaving column (7). The cooled and partly condensed gas mixture which entered via line (8) leaves the heat exchanger (9) via line (11) to a water-cooled condenser (12) in which it is cooled to about 35° C. The material liquefied here goes via line (13) to the phase separator (14) where it is collected. The proportion of liquid exceeding a particular level in the phase separator (14) is pumped by means of the pump (15) via line (16), back into the predewatering column (7). After some time, the condensate obtained in the phase separator (14) separates into two phases (17) and (18), of which the aqueous phase (17) is discharged via line (19) and only the organic phase (18) is pumped back partly via line (16), as reflux to the top of the predewatering column (7). The organic phase (18) is also partly transferred via line (55) to the depressurization vessel (56).

The gas mixture leaving the condenser (12) via line (20) is scrubbed and freed of uncondensed vinyl acetate in the scrubbing column (21) (recycle gas scrubber) by means of the acetic acid introduced via line (51). The bottoms from the recycle gas scrubber (21) are separated, with a substream being circulated by pumping via line (22) and recirculated with cooling by means of the heat exchanger (23) to the lower part of the recycle gas scrubber (21) and the other part of the bottoms being conveyed via line (24) through a heat exchanger (25) in which the bottoms are heated to a temperature of from 60 to 100° C. The bottom product which has been heated in this way is subsequently pumped back to the lower part of the predewatering column (7), at the $5^{th}$ to $10^{th}$ plate, calculated from the bottom of the column.

The tailgas or recycle gas (ethylene, unreacted oxygen and $CO_2$ formed as by-product) leaving the scrubbing column (21) via line (26) is combined with the flash gas comprising predominantly ethylene and additionally $CO_2$, inerts such as nitrogen and argon and also acetic acid and small amounts of vinyl acetate and ethyl acetate which is brought via flash gas line (35) into line (10). Additionally, fresh ethylene is introduced via line (29) as well as recycle gas with reduced amount of $CO_2$ is introduced via line (73) into line (10) which enters into the countercurrent heat exchanger (9) where the gas stream is heated. The preheated gas stream leaves heat exchanger (9) via line (70) is compressed by means of the recycle gas compressor (27) and recirculated via line (1) and the acetic acid vaporizer (2) to the reactor (5). Part of the recycle gas is removed as offgas via line (71) to discharge $CO_2$ in the $CO_2$ removal system (72). The $CO_2$ removal system has a design known per se. In general the $CO_2$ removal system is a scrubber. The $CO_2$ removal comprises a cooling step which is followed by a washing step with acetic acid and subsequently a washing step with water. The washing steps are followed by the $CO_2$ absorption step, e.g. treatment with potassium hydroxide. To avoid the introduction of water vapour in the recycle gas the recycle gas with the reduced amount of $CO_2$ leaving the $CO_2$ removing system (72) via line (73) is cooled, preferably to a temperature of 10 to 60° C., more preferably 20 to 40° C.

The liquid obtained at the bottom of the predewatering column (7), which comprises mainly vinyl acetate, acetic acid and water and contains virtually all the ethyl acetate, is fed via line (31) to a vessel (32), also referred to as crude vinyl acetate collection vessel, and depressurized there, to a pressure of from 0.1 to 0.15 MPa. The flash gas formed here, which comprises predominantly ethylene and additionally $CO_2$, inerts such as nitrogen and argon and also organic constituents such as acetic acid is discharged via line (33), combined with the recycled gas brought via line (57), which has approximately the same composition, and, after compression in the flash gas compressor (34), combined via line (35) with the recycle gas from the recycle gas scrubber (21) brought via line (26) into line (10). The organic phase obtained after depressurization in the crude vinyl acetate collection vessel (32) is taken off via the line (36) and introduced into the second distillation column (37), also referred to as azeotrope column.

The vapor from the top of the second distillation column (37) is conveyed via line (38) to the condenser (39) and condensed there. The condensate fed via line (40) to the phase separator (41) separates into an aqueous phase (42) which is taken off via line (43) and an organic phase (44) which is combined with the organic phase brought via line (58). The organic phase combined in the phase separator (41) is discharged by means of the pump (45). Part of the organic phase discharged is fed via line (46) to the top of the azeotrope column (37) and serves as reflux there. The part which is not used as reflux is discharged via line (47) and fed to a third distillation column (48), viz. the dewatering column. The ethyl acetate introduced via line (36) into column (37) is taken off from an enrichment zone above the bottom of the column (37) via line (49). The bottom product from the column (37) comprises virtually all the acetic acid obtained in the vinyl acetate work-up, not more than 10% by weight of water and also small amounts of high boilers and polymers and only traces of vinyl acetate and ethyl acetate.

The aqueous acetic acid is taken off from the bottom of the column (37) via the line (50) and divided. Depending on the design of the scrubbing column (21) and the temperature of the gas to be scrubbed, differing amounts of acetic acid are required as scrubbing liquid. The proportion required for the acetic acid scrub is fed via line (51) and the pump (52) to the scrubbing column (21). The remainder is fed via the pump (53) and line (3) to the acetic acid vaporizer (2). Fresh acetic acid is fed in an amount corresponding to the amount of acetic acid consumed in the reaction to the top of the acetic acid vaporizer (2) via line (54) and simultaneously serves as scrubbing solution for the recovered acetic acid brought via line (3), also referred to as recycle acetic acid.

The remainder of the organic phase (18) from the phase separator (14) is, if not all of the organic phase (18) is used as reflux in the predewatering column (7), fed via line (55) to the depressurization vessel (56). The recycle gas formed during the depressurization to a pressure of from 0.02 to 0.2 MPa is discharged via line (57), combined with the recycle gas brought via line (33) and, after compression by means of the recycle gas compressor (34), recirculated to the process via line (35).

The liquid obtained in the vessel (56) is fed via line (58) to the phase separator (41) from where the combined organic phases are partly fed as reflux via line (46) to the azeotrope column (37) and partly as feed via line (47) to the third distillation column (48), also referred to as dewatering column. The feed to the dewatering column is virtually free of acetic acid.

The low boilers and last residues of water present in the vapor from the top of the column (48) are conveyed away via the line (59) and discharged from the work-up process.

The virtually water-free vinyl acetate obtained at the bottom of the column (48) is fed via line (60) to the fourth distillation column (61), also referred to as pure vinyl acetate column. The vapor from the top of this column goes via line (62) to the condenser (63). The condensate obtained is pure vinyl acetate which is free of ethyl acetate. A very small part of this vinyl acetate is recirculated as reflux to the column (61) via line (64). Pure vinyl acetate is taken off via line (65). The bottom product from the column (61), which contains small amounts of ethyl acetate, polymers and high boilers, is recirculated via line (66) and the pump (67) to the column (37). From the acetic acid vaporizer (2), to which all high boilers and polymers are finally recirculated, a substream is taken off via line (67) to discharge polymers/heavy end products.

According to a preferred embodiment, a measure important to the work-up process of the invention is the recirculation of the heated, acetic-acid bottoms from the scrubbing column (21) to the lower part of the predewatering column (7), with the previously heated, acetic-acid bottoms from the scrubbing column being heated once more. This measure is associated with a variety of advantages.

This measure results in a reduction in the solubility of the gaseous components, in particular ethylene and carbon dioxide, which are present in the outflow from the bottom of the recycle gas scrubber and are driven off via the top of the first distillation column and are returned to the recycle gas at an early stage of the process.

As a result, less recycle gas is obtained in the depressurization and this is compressed with lower energy consumption in the recycle gas compressor (34) and returned to the process. The load on the recycle gas compressor is thus reduced.

The introduction of the heated, acetic-acid bottoms from the scrubbing column (21) into the lower part of the predewatering column (7) achieves a scrubbing effect and virtually all of the ethyl acetate is scrubbed into the bottom of the predewatering column (7) and discharged via the bottoms. Only a very small amount of ethyl acetate is carried into the organic phase (18) which collects in the collection vessel (14). The stream taken off via line (55) therefore contains hardly any ethyl acetate. A larger amount of this can therefore be allowed compared to the known mode of operation, as a result of which the loading of the azeotrope column (37) is reduced, which likewise leads to further energy savings. Thus, the azeotrope column can be operated at a significantly lower reflux ratio.

Likewise, a larger amount of water is discharged via the top of the predewatering column (7), as a result of which the amount of water obtained in the vessel (14) can be increased. The removal of water via the predewatering column (7) can therefore be operated more effectively. Water is thus removed to a greater degree at an early stage of the process and the load on later process stages for water removal is reduced.

Furthermore, all of the acetic acid is discharged with the bottoms from the azeotrope column (37), so that the feed to the dewatering column (48) and thus also to the pure vinyl acetate column (61) is virtually free of acetic acid. Corrosion phenomena caused by acetic acid in these parts of the plant can therefore be avoided and it is possible to employ a smaller quantity of corrosion-resistant materials. The avoidance of an acetic acid content in the feed to the pure vinyl acetate column (61) also reduces the outlay for the distillation to isolate the pure vinyl acetate, since the removal of residual traces of acetic acid from vinyl acetate is very difficult. The distillation to isolate the pure vinyl acetate can therefore be operated with a lower energy input and at a lower reflux ratio, which generally means a considerable saving of steam.

EXAMPLE

The process according to the present invention is conducted in accordance with the embodiment depicted in the Figure. The process according to the present invention is compared with the process described in FIG. 1 of EP-A1-1 760 065.

Operated under full load the countercurrent heat exchanger (9) heats the recycle gas together with the fresh ethylene, the recycle gas coming from the $CO_2$ removal system (72) and the flash gas up to 50 K. Thus, up to 4300 kW of the gas stream coming from the predewatering column (7) can be transferred to the recycle gas stream (10) before entering the recycle gas compressor (27). 4300 kW corresponds to 7.4 to/h steam.

The preheated gas stream leaving countercurrent heat exchanger (9) via line (70) is transferred after compression by the recycle gas compressor (27) to the vinyl acetate reactor (5) and subsequently to the predewatering column (7). Due to the increase of the temperature of the recycle gas the reflux at the predewatering column (7) is increased and, as a consequence, more water is discharged since less water is transferred to the second distillation column (azeotrope column (37)). Therefore, at the azeotrope column less steam is required.

The following Table demonstrates the reduced steam consumption of the process according to the present invention compared to the process according to FIG. 1 of EP-A1-1 760 065.

TABLE

| | Amount of recycle gas to the recycle gas compressor (27) | Temperature of the top of scrubbing column (21) | Energy transferred at the countercurrent heat exchanger (9) | Reduction of steam composition |
|---|---|---|---|---|
| Normal load | 180 to/h | 38° C. | 3050 KW | 5.2 to/h |

Additionally, the consumption of cooling water at condenser (12) is significantly reduced. Operated under full load a reduction of the cooling water of 800 m³/h has been observed.

Compared to the process disclosed in FIG. 1 of EP-A1-1 760 065 a reduction of the energy consumption of approximately 20% and a reduction of the steam consumption under full load conditions of approximately 22% could be observed.

We claim:

1. A process for the separation of vinyl acetate from a gas mixture formed by the reaction of ethylene with acetic acid and oxygen in the gas phase over catalysts comprising palladium or palladium compounds comprising:

a) introducing said gas mixture leaving a vinyl acetate reactor into a predewatering column, b) cooling a gas mixture leaving the top of the predewatering column below 85° C. in a countercurrent heat exchanger, c) further cooling a gas mixture or a gas and liquid mixture leaving the heat exchanger in step b) to from −20 to 50° C. to form a condensate that separates into an aqueous phase and an organic phase, d) taking off the aqueous phase formed in step c), e) recirculating all or part of the organic phase formed in step c) as reflux to the top of the predewatering column utilized in step a) and taking off part of the organic phase which is not used as reflux, f) scrubbing a gas comprising vinyl acetate which is not condensed in step c) in a gas scrubbing column by means of an aqueous acetic acid solution, g) isolating the vinyl acetate, h) heating recycle gas leaving the gas scrubbing column, optionally together with fresh ethylene and/or recycle gas coming from a $CO_2$ removal system and/or flash gas, in the countercurrent heat exchanger, with the gas mixture leaving the top of the predewatering column, and thereby reducing the temperature of the gas mixture leaving the top of the predewatering column, and i) introducing the heated recycle gas optionally together with the fresh ethylene and/or the recycle gas coming from the $CO_2$ removal system and/or the flash gas preheated in step h), into the vinyl acetate reactor.

2. A process according to claim 1, wherein step c) is conducted with a water-cooled condenser in which the gas mixture or the gas and liquid mixture is cooled to less than 35° C.

3. A process according to claim 1, wherein the part of the organic phase which is not used as reflux in step e) is transferred to a depressurization vessel.

4. A process according to claim 1, wherein the bottoms of the gas scrubbing column used in step f) is separated with a substream and recirculated with cooling by means of the heat exchanger to the lower part of the gas scrubbing column.

5. A process according to claim 4, wherein the other part of the bottom is conveyed through a heat exchanger and is heated to at least 30° C., and wherein the heated bottoms is conveyed to the lower part of the predewatering column.

6. A process according to claim 5, wherein the heated bottoms is conveyed to the lower part of the predewatering column at the $2^{nd}$ to $15^{th}$ plate, calculated from the bottom.

7. A process according to claim 4, wherein the other part of the bottoms is conveyed through a heat exchanger and is heated to at least 30° C.

8. A process according to claim 4, wherein the other part of the bottoms is conveyed through a heat exchanger and is heated to at least 60 to 120° C.

9. A process according to claim 1, wherein the stream which enters the countercurrent heat exchanger in step h) has a temperature of 10 to 60° C.

10. A process according to claim 9, wherein the stream which enters the countercurrent heat exchanger in step h) comprises fresh ethylene having a temperature before entering the stream of −20 to 40° C.

11. A process according to claim 10, wherein the stream which enters the countercurrent heat exchanger in step h) comprises fresh ethylene having a temperature before entering the stream of −20 to 10° C.

12. A process according to claim 9, wherein the stream which enters the countercurrent heat exchanger in step h) has a temperature from 20 to 40° C.

13. A process according to claim 1, wherein a preheated stream in step h) leaving the countercurrent heat exchanger has a temperature of 50 to 90° C.

14. A process according to claim 13, wherein the preheated stream in step h) leaving the countercurrent heat exchanger has a temperature of 65 to 80° C.

15. A process according to claim 1, wherein a part of the preheated stream in step h) leaving the countercurrent heat exchanger is removed as off gas to discharge $CO_2$ in a $CO_2$ removal system.

16. A process according to claim 15, wherein a gas stream leaving the $CO_2$ removal system enters the recycle gas stream and has a temperature of 10 to 60° C.

17. A process according to claim 16, wherein the gas stream leaving the $CO_2$ removal system and entering the recycle gas stream has a temperature of 20 to 40° C.

18. A process according to claim 1, wherein the heated recycle gas in step h) leaving the countercurrent heat exchanger enters a recycle gas compressor from a suction side.

19. A process according to claim 1, wherein a liquid obtained at the bottom of the predewatering column which comprises vinyl acetate, acetic acid, water and ethyl acetate is depressurized to a pressure of from 0.02 to 0.2 MPa to form flash gas.

20. A process according to claim 19, wherein the depressurized liquid is introduced into an azeotrope distillation column.

21. A process according to claim 19, wherein the liquid obtained at the bottom of the predewatering column is depressurized to a pressure of from 0.1 to 0.15 MPa to form the flash gas.

22. A process according to claim 1, wherein the gas mixture leaving the top of the predewatering column is cooled to a temperature below 80° C.

23. A process according to claim 1, wherein the gas mixture leaving the top of the predewatering column is cooled to a temperature between 55° C. and 75° C.

\* \* \* \* \*